United States Patent
Wolf et al.

[11] Patent Number: 6,031,710
[45] Date of Patent: *Feb. 29, 2000

[54] ADHESIVELY- AND SOLDER-BONDED CAPACITIVE FILTER FEEDTHROUGH FOR IMPLANTABLE MEDICAL DEVICES

[75] Inventors: William D. Wolf, St. Louis Park; Mary A. Fraley, Minnetonka; Lynn M. Seifried; Ronald F. Hoch, both of Minneapolis, all of Minn.

[73] Assignee: Medtronic, Inc., Minneapolis, Minn.

[ * ] Notice: This patent is subject to a terminal disclaimer.

[21] Appl. No.: 08/993,974

[22] Filed: Dec. 18, 1997

Related U.S. Application Data

[63] Continuation-in-part of application No. 08/852,198, May 6, 1997, Pat. No. 5,870,272.

[51] Int. Cl.[7] .............................. H01G 4/35; H01G 4/008
[52] U.S. Cl. ........................ 361/302; 361/307; 361/329; 361/305; 174/152 GM; 333/182; 333/185; 29/25.42
[58] Field of Search ...................................... 361/302, 303, 361/305, 306.1, 306.2, 306.3, 307, 309, 311, 329, 330, 328; 29/25.42, 842, 844; 174/50.51, 50.56, 50.63, 143; 333/181, 182, 183, 184, 185; 607/36.5

[56] References Cited

U.S. PATENT DOCUMENTS

| | | |
|---|---|---|
| 1,180,614 | 4/1916 | Simpson . |
| 2,756,375 | 7/1956 | Peck . |
| 3,235,939 | 2/1966 | Rodriguez et al. . |
| 3,266,121 | 8/1966 | Rayburn . |
| 3,304,362 | 2/1967 | August . |
| 3,538,464 | 11/1970 | Walsh . |
| 3,624,460 | 11/1971 | Correll ..................................... 317/230 |
| 3,844,921 | 10/1974 | Benedict ................................. 204/196 |
| 3,920,888 | 11/1975 | Barr ................................. 174/152 GM |
| 4,010,759 | 3/1977 | Boer ..................................... 128/419 P |
| 4,015,175 | 3/1977 | Kendall et al. .......................... 361/313 |
| 4,041,587 | 8/1977 | Kraus ....................................... 29/25.42 |
| 4,083,022 | 4/1978 | Nijman ...................................... 333/79 |
| 4,107,762 | 8/1978 | Shirm et al. ............................. 361/433 |
| 4,148,003 | 4/1979 | Colburn et al. ......................... 333/181 |
| 4,152,540 | 5/1979 | Duncan et al. .......................... 174/152 |
| 4,168,351 | 9/1979 | Taylor ....................................... 429/48 |
| 4,220,813 | 9/1980 | Kyle ........................................ 174/152 |
| 4,247,881 | 1/1981 | Coleman ................................. 361/302 |
| 4,314,213 | 2/1982 | Wakino .................................. 333/182 |
| 4,352,951 | 10/1982 | Kyle .................................. 174/152 GM |
| 4,362,792 | 12/1982 | Bowsky et al. .......................... 429/181 |
| 4,421,947 | 12/1983 | Kyle ........................................ 174/152 |
| 4,424,551 | 1/1984 | Stevenson et al. ...................... 361/302 |

(List continued on next page.)

FOREIGN PATENT DOCUMENTS

| | | |
|---|---|---|
| 0 331 959 A2 | 2/1989 | European Pat. Off. . |
| 0 331 959 A3 | 2/1989 | European Pat. Off. . |
| 28 15 118 | 10/1978 | Germany . |

*Primary Examiner*—Kristine Kincaid
*Assistant Examiner*—Eric W. Thomas
*Attorney, Agent, or Firm*—Thomas F. Woods; Harold R. Patton

[57] ABSTRACT

A capacitive filter feedthrough assembly and method of making same are disclosed for shielding an implantable medical device such as pacemaker or defibrillator from electromagnetic interference or noise. A ferrule is adapted for mounting onto a conductive device housing by welding, soldering, brazing or gluing, and supports a terminal pin for feedthrough passage to a housing interior. A capacitive filter is mounted at the inboard side of a device housing, with capacitive filter electrode plate sets coupled respectively to the housing and the terminal pin by an electrically conductive combination of adhesive, brazing and soldering. In one embodiment of the invention, multiple capacitive filters are provided in an array within a common base structure, where each capacitive filter is associated with a respective terminal pin.

22 Claims, 8 Drawing Sheets

U.S. PATENT DOCUMENTS

| | | | |
|---|---|---|---|
| 4,456,786 | 6/1984 | Kyle | 174/152 |
| 4,556,613 | 12/1985 | Taylor et al. | 429/101 |
| 4,683,516 | 7/1987 | Miller | 361/328 |
| 4,737,601 | 4/1988 | Gartzke | 174/152 GM |
| 4,741,710 | 5/1988 | Hogan et al. | 439/620 |
| 4,791,391 | 12/1988 | Linnell et al. | 333/184 |
| 4,934,366 | 6/1990 | Truex et al. | 128/419 P |
| 5,032,692 | 7/1991 | DeVolder | 174/52.3 |
| 5,070,605 | 12/1991 | Daglow et al. | 29/842 |
| 5,104,755 | 4/1992 | Taylor et al. | 429/181 |
| 5,144,946 | 9/1992 | Weinberg et al. | 178/419 P |
| 5,333,095 | 7/1994 | Stevenson et al. | 361/302 |
| 5,406,444 | 4/1995 | Seifried et al. | 361/302 |
| 5,440,447 | 8/1995 | Shipman et al. . | |
| 5,531,003 | 7/1996 | Seifried et al. | 29/25.42 |
| 5,535,097 | 7/1996 | Ruben et al. | 361/736 |
| 5,620,476 | 4/1997 | Truex et al. | 607/36 |
| 5,650,759 | 7/1997 | Hittman et al. . | |
| 5,870,272 | 2/1999 | Seifried et al. | 361/302 |

ADHESIVELY- AND SOLDER-BONDED CAPACITIVE FILTER FEEDTHROUGH FOR IMPLANTABLE MEDICAL DEVICES

This application is a Continuation-in-Part of application Ser. No. 08/852,198 filed May 6, 1997 now U.S. Pat. No. 5,870,272.

FIELD OF THE INVENTION

This invention relates to electrical feedthroughs of improved design and to their method of fabrication.

BACKGROUND OF THE INVENTION

Electrical feedthroughs serve the purpose of providing an electrical circuit path extending from the interior of a hermetically sealed container to an external point outside the container. A conductive path is provided through the feedthrough by a conductor pin which is electrically insulated from the container. Many such feedthroughs are known in the art which provide the electrical path and seal the electrical container from its ambient environment. Such feedthroughs typically include a ferrule, the conductor pin or lead and a hermetic glass or ceramic seal which supports the pin within the ferrule. Such feedthroughs are typically used in electrical medical devices such as implantable pulse generators (IPGs). It has recently been discovered that such electrical devices can, under some circumstances, be susceptible to electromagnetic interference (EMI). At certain frequencies for example, EMI can inhibit pacing in an IPG. This problem has been addressed by incorporating a capacitor structure within the feedthrough ferrule, thus shunting any EMI at the entrance to the IPG for high frequencies. This has been accomplished with the aforementioned capacitor device by combining it with the feedthrough and incorporating it directly into the feedthrough ferrule. Typically, the capacitor electrically contacts the pin lead and the ferrule.

Some of the more popular materials employed to form the pin lead include tantalum and niobium. Unfortunately, tantalum and niobium are susceptible to oxide growth which can, depending on its extent, act as an insulator instead of a conductor over the surface of the pin lead. During fabrication of a feedthrough and capacitor combination, the pin is subjected to one or more heat treatments which can encourage oxidation, affecting the conductivity of the pin lead and its ability to make good electrical connections between other elements including the capacitor and so forth.

Many different insulator structures and related mounting methods are known in the art for use in medical devices wherein the insulator structure also provides a hermetic seal to prevent entry of body fluids into the housing of the medical device. However, the feedthrough terminal pins are connected to one or more lead wires which effectively act as an antenna and thus tend to collect stray or electromagnetic interference (EMI) signals for transmission to the interior of the medical device. In some prior art devices, ceramic chip capacitors are added to the internal electronics to filter and thus control the effects of such interference signals. This internal, so-called "on-board" filtering technique has potentially serious disadvantages due to intrinsic parasitic resonances of the chip capacitors and EMI radiation entering the interior of the device housing.

In another and normally preferred approach, a filter capacitor is combined directly with a terminal pin assembly to decouple interference signals to the housing of the medical device. In a typical construction, a coaxial feedthrough filter capacitor is connected to a feedthrough assembly to suppress and decouple undesired interference or noise transmission along a terminal pin.

So-called discoidal capacitors having two sets of electrode plates embedded in spaced relation within an insulative substrate or base typically form a ceramic monolith in such capacitors. One set of the electrode plates is electrically connected at an inner diameter surface of the discoidal structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing or case of the electronic instrument.

In operation, the discoidal capacitor permits passage of relatively low frequency electrical signals along the terminal pin, while shunting and shielding undesired interference signals of typically high frequency to the conductive housing. Feedthrough capacitors of this general type are commonly employed in implantable pacemakers, defibrillators and the like, wherein a device housing is constructed from a conductive biocompatible metal such as titanium and is electrically coupled to the feedthrough filter capacitor. The filter capacitor and terminal pin assembly prevent interference signals from entering the interior of the device housing, where such interference signals might otherwise adversely affect a desired function such as pacing or defibrillating.

In the past, feedthrough filter capacitors for heart pacemakers and the like have typically been constructed by preassembly of the discoidal capacitor with a terminal pin subassembly which includes the conductive terminal pin and ferrule. More specifically, the terminal pin subassembly is prefabricated to include one or more conductive terminal pins supported within the conductive ferrule by means of a hermetically sealed insulator ring or bead. See, for example, the terminal pin subassemblies disclosed in U.S. Pat. Nos. 3,920,888, 4,152,540; 4,421,947; and 4,424,5511. The terminal pin subassembly thus defines a small annular space or gap disposed radially between the inner terminal pin and the outer ferrule. A small discoidal capacitor of appropriate size and shape is then installed into this annular space or gap, in conductive relation with the terminal pin and ferrule, by means of soldering, conductive adhesive, etc. The thus-constructed feedthrough capacitor assembly is then mounted within an opening in the pacemaker housing, with the conductive ferrule in electrical and hermetically sealed relation in respect of the housing, shield or container of the medical device.

Although feedthrough filter capacitor assemblies of the type described above have performed in a generally satisfactory manner, the manufacture and installation of such filter capacitor assemblies has been relatively costly and difficult. For example, installation of the discoidal capacitor into the small annular space between the terminal pin and ferrule can be a difficult and complex multi-step procedure to ensure formation of reliable, high quality electrical connections. Moreover, installation of the capacitor at this location inherently limits the capacitor to a small size and thus also limits the capacitance thereof. Similarly, subsequent attachment of the conductive ferrule to the pacemaker housing, typically by welding or brazing processes or the like, can expose the fragile ceramic discoidal capacitor to temperature variations sufficient to create the risk of capacitor cracking and failure.

There exists, therefore, a significant need for improvements in feedthrough filter capacitor assemblies of the type used, for example, in implantable medical devices such as heart pacemakers and the like, wherein the filter capacitor is designed for relatively simplified and economical, yet highly reliable, installation. In addition, there exists a need for an improved feedthrough assembly having a discoidal capacitor which can be designed to provide a significantly increased capacitance for improved filtering. The present invention fulfills these needs and provides further advantages.

Disclosures relating to implantable medical devices, feedthroughs and capacitive filtering of EMI include the patents listed below in Table 1.

TABLE 1

Prior Art Patents

U.S. Patents

| | | | |
|---|---|---|---|
| 1,180,614 | 4/1916 | Simpson | 428/662 |
| 2,756,375 | 7/1956 | Peck | 361/302 |
| 3,266,121 | 8/1966 | Rayburn | 29/25.42 |
| 3,235,939 | 2/1966 | Rodriguez et al. | 29/25.42 |
| 3,304,362 | 2/1967 | August | 174/50.61 |
| 3,538,464 | 11/1970 | Walsh | 361/302 X |
| 3,624,460 | 11/1971 | Correll | 29/25.03 X |
| 3,844,921 | 10/1974 | Benedict | 204/196 |
| 3,920,888 | 11/1975 | Barr | 174/152GM |
| 4,010,759 | 3/1977 | Boer | 174/152GM X |
| 4,015,175 | 3/1977 | Kendall et al. | 361/313 |
| 4,041,587 | 8/1977 | Kraus | 29/25.42 |
| 4,083,022 | 4/1978 | Nijman | 333/185 |
| 4,107,762 | 8/1978 | Shirn et al. | 29/25.04 X |
| 4,148,003 | 4/1979 | Colburn et al. | 361/302 |
| 4,152,540 | 5/1979 | Duncan et al. | 174/152GM |
| 4,168,351 | 9/1979 | Taylor | 333/182 |
| 4,220,813 | 9/1980 | Kyle | 174/152GM |
| 4,247,881 | 1/1981 | Coleman | 361/302 |
| 4,314,213 | 2/1982 | Wakino | 361/302 |
| 4,352,951 | 10/1982 | Kyle | 174/152GM |
| 4,362,792 | 12/1982 | Bowsky et al. | 174/152GM |
| 4,421,947 | 12/1983 | Kyle | 174/152GM |
| 4,424,551 | 1/1984 | Stevenson | 361/302 |
| 4,456,786 | 6/1984 | Kyle | 174/152GM |
| 4,556,613 | 12/1985 | Taylor et al. | 429/101 |
| 4,683,516 | 7/1987 | Miller | 361/328 |
| 4,737,601 | 4/1988 | Gartzke | 174/152GM |
| 4,741,710 | 5/1988 | Hogan et al. | 333/185 |
| 4,791,391 | 12/1988 | Linnell | 361/302 |
| 4,934,366 | 9/1989 | Truex et al. | 128/419 |
| 5,032,692 | 7/1991 | DeVolder | 361/30.2 |
| 5,070,605 | 12/1991 | Daglow et al. | 29/842 |
| 5,104,755 | 4/1992 | Taylor et al. | 174/50.61 |
| 5,144,946 | 9/1992 | Weinberg et al. | 178/419 |
| 5,333,095 | 7/1994 | Stevenson et al. | 29/25.42 X |
| 5,406,444 | 4/1995 | Seifried | 361/302 |
| 5,440,447 | 8/1995 | Shipman et al. | 361/302 |
| 5,531,003 | 7/1996 | Seifried | 29/25.42 |
| 5,535,097 | 7/1996 | Ruben | 361/736 |

Foreign Patents

| | | | |
|---|---|---|---|
| 2815118 | 10/1978 | Fed. Rep. of Ger. | 361/302 |
| 0331959 | 9/1989 | E.P.O. | |
| 892492 | 2/1981 | U.S.S.R. | 29/25.42 |

As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

SUMMARY OF THE INVENTION

The present invention has certain objects. That is, the present invention provides solutions to at least some of the problems existing in the prior art respecting capacitive filters in feedthrough assemblies.

The present invention provides solutions to at least some of the problems associated with conventional capacitive filter feedthrough assembly designs where a discoidal capacitor is placed within ferrule walls, such as in U.S. Pat. Nos. 4,424,551 and 5,333,095. At least some aspects of known capacitive filter feedthrough assemblies may be characterized generally as:

(a) involving difficult to implement conductive epoxy placement steps;

(b) having high electrical resistances at refractory metal interfaces owing to the presence of conductive epoxy and undesirable metal oxides;

(c) exhibiting poor or variable electrical performance in respect of EMI signal attenuation;

(d) requiring multiple labor intensive manufacturing processing steps;

(e) having through pins which cannot be wire bonded to, or are difficult to wire bond to;

(f) exhibiting electrical shorts owing to uncontrolled or inaccurate epoxy placement;

(g) having capacitors crack owing to differing thermal expansion coefficients of the conductive can, the capacitor or the electrically conductive epoxy commonly employed to attach the capacitor to a ferrule or container;

(h) providing no opportunity for visual inspection of the feedthrough assembly once installed in the device;

(I) not permitting the use of registration or centering elements during the manufacturing process, or (j) exhibiting poor mechanical joint strength.

The present invention provides solutions to at least some of the problems associated with conventional capacitive filter feedthrough assembly designs where a capacitor is placed to one side of a feedthrough such as in U.S. Pat. No. 5,333,095. Capacitive filter feedthrough assemblies disclosed in the '095 patent may be characterized generally as:

(a) not permitting the use of registrations or centering elements;

(b) having through pins which cannot be wire bonded to, or are difficult to wire bond to;

(c) having capacitors crack owing to differing thermal expansion coefficients of the conductive can and the capacitor;

(d) exhibiting poor mechanical joint strength.

The present invention provides solutions to at least some of the problems associated with conventional capacitive filter feedthrough assembly designs where solder is employed to connect a capacitor to a feedthrough. Capacitive filter feedthrough assemblies of the type employing solder to connect capacitors to feedthroughs are generally characterized in the use of flux to solder a capacitor to a feedthrough. The use of flux increases the number of manufacturing steps required to make a device because of the requisite cleaning attending the use of flux. Cleaning is required when using flux because otherwise degradation of the hermetic seal can occur due to the presence of moisture and corrosive ionic components in flux material.

Some embodiments of the present invention provide certain advantages which include, but are not limited to:

(a) permitting the attachment of a capacitive filter to gold brazing;

(b) increasing the electrical conductivity between a capacitive filter and a feedthrough;

(c) increasing the EMI filtering capability provided for an implantable medical device;

(d) eliminating the presence of electrically resistive metal oxides between a capacitive filter and a shield or feedthrough;
(e) requiring only one method for connecting a capacitive filter to a pin or ferrule;
(f) eliminating secondary manufacturing process steps such as epoxy application or additional soldering steps;
(g) reducing manufacturing costs;
(h) reducing implantable medical device costs;
(I) enclosing a capacitive filter at least partially in a ferrule to thereby provide additional mechanical support to the filter;
(j) eliminating secondary cleaning steps associated with soldering;
(k) permitting the use of a capacitive filter having higher capacitances than chip capacitors, and therefore providing enhanced EMI filtering capability;
(l) providing a protruding upper capacitive filter wire bond pad suitable for wire bonding thereto;
(m) preventing chipping or abrasion of a capacitive filter due to pass-through pin bending, and
(n) permitting the use of sputtered capacitors, and
(o) permitting the use of low temperature solders having increased ductility and enhanced corrosion resistance.

Some embodiments of the present invention have certain features, including, but not limited to:
(a) a capacitive filter that is at least partially disposed within or surrounded by first sidewalls forming a first aperture in a ferrule;
(b) a capacitive filter that is surface mounted or otherwise disposed atop a ferrule, the filter not being disposed within the first aperture, or not being surrounded by the first sidewalls;
(c) a pin having an upper portion, the upper portion extending upwardly into a second aperture in an insulator, the pin being electrically and mechanically connected to a contact pad extending downwardly into a third aperture of the capacitive filter;
(d) a pin, the upper portion thereof extending through or substantially through the second aperture, the upper portion optionally extending through or substantially through the first aperture;
(e) a feedthrough assembly having no contact pad disposed within the first ferrule, where electrical and mechanical connection of internal circuitry to the pin of the assembly is accomplished by attaching an electrical conductor in or to the third aperture of the capacitive filter, the filter being disposed within or atop the first aperture;
(f) inner braze joints, intermediate braze joints, and/or outer braze joints formed of: (I) pure gold; (ii) gold alloys comprising gold and at least one of titanium, niobium, vanadium, nickel, molybdenum, platinum, palladium, ruthenium, silver, rhodium, osmium, iridium, and alloys, mixtures and thereof; (iii) copper-silver alloys, including copper-silver eutectic alloys, comprising copper and silver and optionally at least one of indium, titanium, tin, gallium, palladium, platinum, and alloys, mixtures and combinations thereof; and (iv) silver-palladium-gallium alloys;
(g) an inner solder joint and/or an outer solder joint electrically and mechanically connected to an inner braze joint and/or an outer braze joint, and/or an inner adhesive joint or an outer adhesive joint, the solder joints being formed of: (i) indium only; (ii) lead only; (iii) silver only; (iv) tin only; (v) indium-silver alloys; (vi) indium-tin alloys; (vii) tin-lead alloys; (viii) tin-silver alloys; (ix) indium-lead-silver alloys; (x) tin-lead-silver alloys, (xi) alloys, mixtures and combinations of (I) through (x); and (xii) gold-containing solders such as: (1) gold-tin alloys; (2) gold-silicon alloys; (3) gold-germanium alloys; (4) gold-indium alloys, and alloys, mixtures and combinations of (1) through (4); and
(h) inner adhesive joints and/or outer adhesive joints electrically and mechanically connected to an inner braze joint and/or an outer braze joint, and/or to an inner solder joint and/or an outer solder joint, the adhesive joints being formed of a suitable, preferably epoxy-based, material, and
(i) at least one capacitive filter having first and second electrical terminals connected electrically and mechanically through braze and adhesive joints, respectively, and optionally through other components to circuitry internal to an implantable medical device and to the implantable medical device case or shield.

DETAILED DESCRIPTION OF THE PREFERRED EMBODIMENTS

Figure 1:
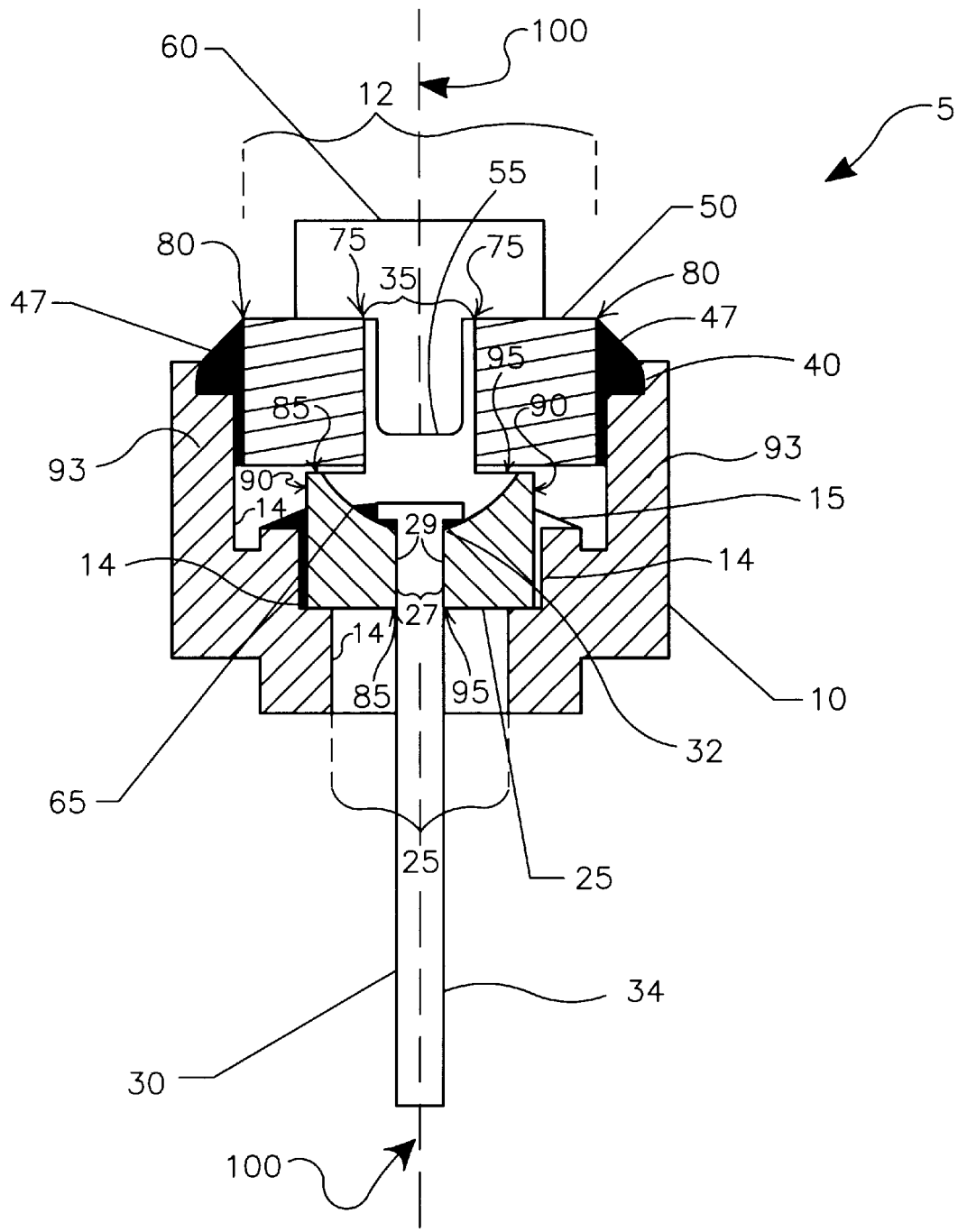
FIG. 1 shows a cross-sectional view of one embodiment of a uni-polar feedthrough assembly of the present invention.

In the claims and specification hereof, the adjective "upper" refers to those portions of feedthrough assembly 5 having contact pad 60 propinquant thereto, the adjective "lower" refers to those portions of feedthrough assembly 5 having pin 30 propinquant thereto, the adjective "inner" refers to those portions of feedthrough assembly 5 having central vertical axis 100 of pin 30 propinquant thereto, and the adjective "outer" refers to those portions of feedthrough assembly 5 having outer surface 80 of capacitive filter 50 propinquant thereto.

We refer to U.S. Pat. No. 4,678,868 to Kraska et al., which discloses brazing techniques suitable for use in feedthrough assemblies in implantable medical devices, at least some of which techniques may be adapted for use in the present invention.

Figure 2:
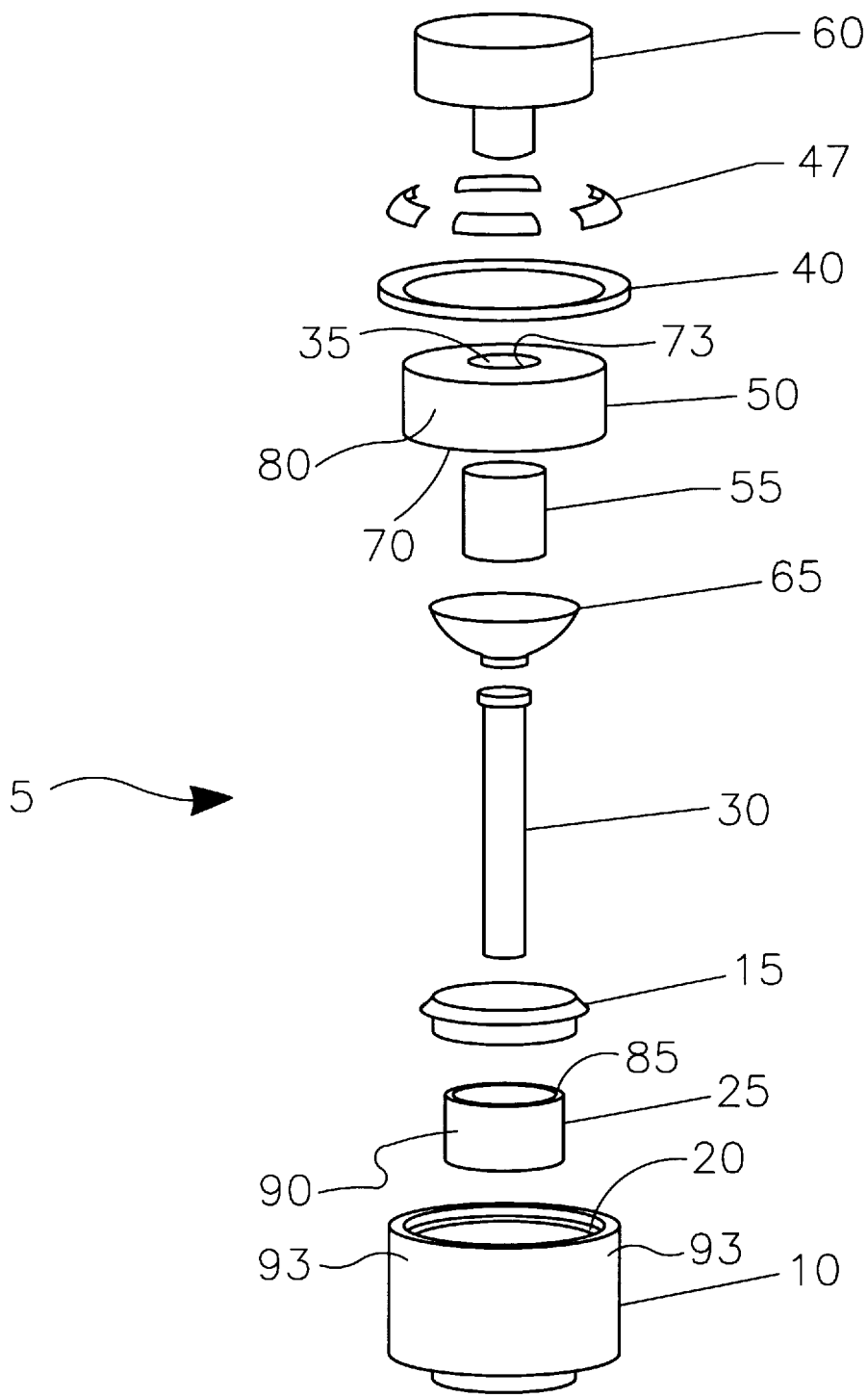
FIG. 2 shows an exploded, perspective view of the uni-polar feedthrough assembly of FIG. 1.

FIG. 1 shows a cross-sectional view of one embodiment of a uni-polar feedthrough assembly 5 of the present invention after being subjected to the brazing and adhesive-bonding steps of the present invention. FIG. 2 shows an exploded, perspective view of the uni-polar feedthrough assembly of FIG. 1.

Electrically conductive ferrule 10 of FIGS. 1 and 2 is preferably welded to shield or container 20 of hermetically sealed implantable medical device 70, and has first aperture 12 disposed therethrough formed by first sidewalls 14. Electrically insulative insulator 25 is disposed within first aperture 12, provides electrical insulation between electrically conductive feedthrough pin 30 and ferrule 10, and has second aperture 27 disposed therethrough formed by second sidewalls 29.

Ferrule 10 is typically laser welded to shield or container 20, and may be formed of niobium, titanium, titanium alloys such as titanium-6AI-4V or titanium-vanadium, platinum, molybdenum, zirconium, tantalum, vanadium, tungsten, iridium, rhodium, rhenium, osmium, ruthenium, palladium, silver, and alloys, mixtures and combinations thereof. Ferrule 10 may be welded by other means to shield or container 20, or even soldered or glued thereto.

Upper portion 32 of electrically conductive pin 30 is disposed within or may extend at least partially into second aperture 27. Lower portion 34 of pin 30 is generally connected to electrical circuitry, connectors or a connector block external to container 20 of device 70, but may alternatively be connected directly to a connector on a medical lead. In one embodiment of the present invention, upper portion 32 of pin 30 extends upwardly into second aperture 27, and is electrically and mechanically connected by inner braze joint 65 and inner adhesive joint 55 to contact pad 60, where contact pad 60 extends downwardly into third aperture 35 of capacitive filter 50.

In another embodiment of the present invention, upper portion 32 of pin 30 extends through or substantially through second aperture 27, and may optionally extend through or substantially through first aperture 12. Upper portion 32 of pin 30 may also be connected directly to an electrical conductor attached to internal circuitry, with no contact pad 60 being disposed in third aperture 35.

Pin 30 may be formed of niobium, titanium, titanium alloys such as titanium-6AI-4V or titanium-vanadium, platinum, molybdenum, zirconium, tantalum, vanadium, tungsten, iridium, rhodium, rhenium, osmium, ruthenium, palladium, silver, and alloys, mixtures and combinations thereof.

Electrically conductive intermediate braze joint 15 most preferably provides an hermetic braze joint and seal between ferrule 10 and insulator 25, and is disposed between at least outer insulator surface 90 and first sidewalls 14 of first aperture 12.

Insulator 25 is most preferably formed of alumina (or aluminum oxide), but may be formed of any suitable electrically insulative, ceramic-containing material comprising, for example, sapphire or zirconium oxide. Under certain circumstances, inner insulator surface 85 and outer insulator surface 90 must have a suitable metal or alloy disposed thereon to permit insulator 25 to be brazed to pin 30 or to ferrule 10.

In a preferred embodiment of the present invention, where pure gold is employed to form inner and intermediate braze joints 65 and 15, a 25,000 Angstrom thick layer of niobium is sputtered onto surfaces 85 and 90 by vacuum deposition using a Model No. 2400 PERKIN-ELMER® sputtering system. The niobium layer is most preferably between about 15,000 and about 32,000 Angstroms thick. Metals other than niobium may be sputtered on surfaces 85 and 90, such as titanium or molybdenum. If metals such as: (i) gold alloys comprising gold and at least one of titanium, niobium, vanadium, nickel, molybdenum, platinum, palladium, ruthenium, silver, rhodium, osmium, iridium, and alloys, mixtures and thereof; (ii) copper-silver alloys, including copper-silver eutectic alloys, comprising copper and silver and optionally at least one of indium, titanium, tin, gallium, palladium, platinum; or (iii) alloys, mixtures or combinations of (i) or (ii) are employed, then metallization of surfaces 85 and 90 may not be required.

Optional electrically conductive outer braze joint 40 provides a platform for the attachment of outer adhesive joint 45 and/or outer solder joint 45 thereto. In preferred embodiments of the present invention, braze joint 40 is disposed between sidewalls 14 of first aperture 12 and outer surface 80 of capacitive filter 50. In other preferred embodiments of the present invention, outer braze 40 is disposed atop ferrule 10 along the top peripheral surface thereof. Outer braze joint 40 need not, but may, provide a hermetic seal.

Electrically conductive outer solder joint 45, may be disposed between ferrule 10 and outer braze joint 40 on the one hand, and a second terminal or electrode of capacitive filter 50 on the other hand, to provide a solder joint therebetween. Outer solder seal 45 need not, but may, provide a hermetic seal. Outer solder joint 45 may permit a second terminal or electrode of capacitor 50 to be mechanically and electrically affixed by solderable means to ferrule 10 through outer braze joint 40.

Electrically conductive inner solder joint 55 may be disposed in third aperture or passageway 35 of capacitor 50 between contact pad 60 and inner braze joint 65, to provide a solder joint therebetween. Inner solder seal 55 need not, but may, provide a hermetic seal. Inner solder joint 55 permits a first terminal or electrode of capacitor 50 to be mechanically and electrically affixed by solderable means to ferrule 10 through inner braze joint 65.

Electrically conductive outer adhesive joint 45 is preferably disposed between ferrule 10 and outer braze joint 40 on the one hand, and a second terminal or electrode of capacitive filter 50 on the other hand, and provides an adhesive joint therebetween. Outer adhesive joint 45 need not, but may, provide a hermetic seal. Outer adhesive joint 45 may be employed to permit a second terminal or electrode of capacitor 50 to be mechanically and electrically affixed by adhesive means to ferrule 10 through outer braze joint 40.

Alternatively, and in a manner not shown in the Figures, outer adhesive joint 45 may be connected to a second terminal or outer surface 80 of filter 50 as follows. Insulator 25 may have a wider outer diameter and ferrule 10 may have a lower profile (or lower or non-existent top portion 93) than those shown in FIGS. 1 and 2, such that the second terminal or outer surface 80 of filter 50 may engage, through outer adhesive joint 45, intermediate braze joint 15. In such a configuration, top portion 93 of ferrule 10 may be eliminated or shortened in height, and outer braze joint 40 may be eliminated altogether. In another embodiment of the present invention not shown in the Figures, outer adhesive joint 45 and/or outer braze joint 40 may be replaced with outer solder joint 45 of the present invention (some suitable compositions of which are more fully described below).

Inner adhesive joint 55 and outer adhesive joint 45 are most preferably formed of the same adhesive material, but may less preferably be formed of different adhesive materials. In preferred embodiments of the present invention, outer adhesive joint 45 and inner adhesive joint 55 are formed of ABLEBOND® 8700 electrically conductive silver-filled epoxy adhesive provided by ABLESTIK LABORATORIES of Rancho Dominguez, Calif. Other suitable electrically conductive glue- or epoxy-based adhesives and other suitable materials may also be employed in the present invention to form joints 55 or 45. Such materials include gold-or copper-filled epoxies, carbon- or graphite-filled epoxies or even electrically conductive plastics acting effectively as adhesive joints after their application and upon cooling, such as at least some of the electrically conductive plastics or polymers disclosed in U.S. Pat. No. 5,685,632 to Schaller et al. for "Electrically Conductive Plastic Light Source."

Inner braze joint 65 provides a braze joint and seal between insulator 25 and pin 30, and further forms a portion of an electrically conductive pathway extending between pin 30 and contact pad 60, the pathway comprising, but not necessarily limited to, pin 30, inner braze joint 65, inner solder joint 55 and contact pad 60. Inner braze joint 65 is disposed atop or at least partially surrounds upper portion 32 of pin 30. Inner braze joint 65 is also disposed between at least a portion of upper portion 32 of pin 30 and second sidewalls 85 (or inner insulator surface 85) of second aperture 27. In another embodiment of the present invention inner adhesive joint 55 replaces or augments inner solder joint 55.

Inner braze joint 65, intermediate braze joint 15 and outer braze joint 40 are most preferably formed of the same metal or alloy, but may less preferably be formed of different metals or alloys. Braze joints 65, 15 and 40 of the present invention are most preferably formed of 99.9% or purer gold, but may also be formed of: (a) gold alloys comprising gold and at least one of titanium, niobium, vanadium, nickel, molybdenum, platinum, palladium, ruthenium, silver, rhodium, osmium, indium, and alloys, mixtures and thereof; (b) copper-silver alloys, including copper-silver eutectic alloys, comprising copper and silver and optionally at least one of indium, titanium, tin, gallium, palladium, platinum, and alloys, mixtures and combinations thereof; and (c) silver-palladium-gallium alloys.

Inner solder joint 55 and outer solder joint 45 most preferably comprise the same or similar metals or alloys, but may less preferably be formed of different or dissimilar metals or alloys. In preferred embodiments of the present invention, inner solder joint 55 and outer solder joint 45 are formed of an indium-lead solder, and most preferably an indium-lead solder comprising, by weight percent, 70% indium and 30% lead. Other metals or alloys for forming inner solder joint 55 and outer solder joint 45 of the present invention include: (a) indium only; (b) lead only; (c) silver only; (d) tin only; (e) indium-silver alloys; (f) indium-tin alloys; (g) tin-lead alloys; (h) tin-silver alloys; (h) indium-lead-silver alloys; (I) tin-lead-silver alloys, and other alloys, mixtures and combinations thereof. Still other metals or alloys for forming inner solder joint 55 and outer solder joint 45 of the present invention include gold-containing solders such as: (a) gold-tin alloys; (b) gold-silicon alloys; (c) gold-germanium alloys; gold-indium alloys, and alloys, mixtures and combinations thereof.

In one embodiment of the present invention, contact pad 60 is electrically connected to internal circuitry disposed within container or shield 20 of hermetically sealed implantable medical device 70, and is also electrically and mechanically connected to pin 30 through inner braze joint 65 and inner solder joint 55. Electrical connection from internal circuitry to contact pad 60 may be established by wire bonding, soldering, welding, laser welding, brazing, gluing or other suitable means.

In another embodiment of the present invention, contact pad 60 is electrically connected to internal circuitry disposed within container or shield 20 of hermetically sealed implantable medical device 70, and is also electrically and mechanically connected to pin 30 through inner braze joint 65 and inner solder joint 55 and/or inner adhesive joint 55. Electrical connection from internal circuitry to contact pad 60 may be established by wire bonding, soldering, welding, laser welding, brazing, gluing or other suitable means.

In still another embodiment of the present invention, no contact pad 60 is disposed within third aperture 35, and electrical and mechanical connection to internal circuitry of device 70 is accomplished by attaching an electrical conductor to inner solder joint 55 or inner adhesive joint 55, or directly to inner braze joint 65, through third aperture 35 by appropriate wire bonding, soldering, welding, laser welding, brazing, gluing or other suitable electrically conductive attachment means.

Contact pad 60 is most preferably formed of KOVAR® (an iron-nickel-cobalt alloy) having electroplated layers of first nickel and then gold disposed on the surface thereof. Contact pad 60 may also be formed of: (a) brass first plated with nickel and then gold; (b) pure gold; (c) suitable gold alloy plated with gold; (d) nickel plated with gold; (e) suitable nickel alloy plated with gold, and (f) pure copper or copper alloy first plated with nickel and then gold. Contact pad 60 must be electrically conductive and have a melting temperature exceeding the melting temperature of the solder employed to form inner adhesive joint 57 or outer adhesive joint 47. Additionally, the metal disposed on the outer surface of contact pad 60 must be compatible with the adhesive employed to form inner adhesive joint 55 and/or outer adhesive joint 45 and/or the solder employed to form outer solder joint 45 and/or inner solder joint 55.

Ceramic-containing capacitive filter 50 attenuates and filters EMI to prevent the passage or propagation thereof into the interior of shield or container 20. Filter 50 has a third aperture or pathway 35 disposed through a portion thereof for electrical and mechanical connection of contact pad 60 to inner adhesive joint 57. Capacitive filter 50 is most preferably disposed at least partially in first aperture 12 such that ferrule 10 imparts additional mechanical integrity to the mechanical connection between filter 50 and ferrule 10. Alternatively, capacitive filter 50 is disposed outside first aperture 12 in surface mount fashion such that first sidewalls 14 do not at least partially surround outer capacitive filter surface 80, or such that capacitive filter 50 is disposed atop ferrule 10.

In such alternative embodiments of the present invention, however, outer adhesive joint 55 and/or outer solder joint 45 may provide a mechanical and electrical bridge between sidewalls 14 of first aperture 12 of ferrule 10 (or intermediate braze joint 15) and the second terminal or electrode of capacitive filter 50 or outer capacitive filter surface 80. In another embodiment of the present invention, outer adhesive joint 45 or outer solder joint 45 provide a mechanical and electrical bridge between optional outer braze joint 40 (or intermediate braze joint 15) and the second terminal or electrode of capacitive filter 50 or outer capacitive filter surface 80.

In preferred embodiments of the present invention, capacitive filter 50 is a discoidal multi-layer ceramic capacitor having a doughnut-like shape and a central cylindrically-shaped aperture 35 disposed through the center thereof. Capacitive filters forming discoidal multi-layer ceramic capacitors finding particularly efficacious application in the present invention are manufactured by AVX CORPORATION of Myrtle Beach, S.C., MAXWELL LABORATORIES of Carson City, Nevada, CERAMIC DEVICE, INC. of Wenatchee, Wash., and SPECTRUM CONTROL, INC. of Erie, Pa.

Capacitive filters 50 comprising barium titanate have been discovered to provide particularly good results in the present invention. Examples of suitable barium titanate formulations or types for making capacitive filter 50 include, but are not limited to, X7R, Z5U and other formulations. Other types of ceramic capacitors may be employed for capacitive filter 50 of the present invention, such as single-layer capacitors, rectangular capacitors, square capacitors, elliptical capacitors, oval capacitors and the like.

In a preferred embodiment of the present invention, capacitive filter 50 is a discoidal multi-layer ceramic capacitor having silver thick films, silver-palladium alloy thick films, or silver-platinum alloy thick films disposed on inner capacitive filter surface 75 and outer capacitive filter surface 80. Such thick films are typically applied by the capacitive filter manufacturer before shipment. Inner capacitive filter surface 75 forms a first electrical terminal or contact of capacitive filter 50.

Outer capacitive filter surface 80 forms a second electrical terminal or contact of capacitive filter 50. When outer capacitive filter surface 80 is electrically connected to shield or container 20 and inner capacitive filter surface is electrically connected to circuitry or connectors external to container 20 of implantable medical device 70 through contact pad 60, capacitive filter 50 is connected in parallel with signals entering device 70, and thereby provides its EMI filtering capability.

Optionally, two more metal layers may be disposed on inner and outer surfaces 75 and 80 having silver thick films, silver-palladium alloy thick films, or silver-platinum alloy thick films disposed thereon to permit attachment of capacitive filter 50 to outer adhesive joint 47 and/or outer solder joint 45 on the one hand, and inner adhesive joint 57 and/or inner solder joint 55 on the other hand. First layers of nickel are preferably sputtered onto the thick films overlying inner surface 75 and outer surface 80. Next, second layers of gold are preferably sputtered onto the previously deposited nickel layers.

The gold layers provide a means for adhesively attaching capacitive filter 50 to inner adhesive joint 57 and/or inner solder joint 55 on the one hand, and outer adhesive joint 47 and/or outer solder joint 45 on the other hand. Metals and alloys other than pure nickel may be employed for forming the first layers. Pure gold is preferred for forming the second layers, but gold of varying purities may less preferably be employed for forming the second layers.

In another embodiment of the present invention, gold, nickel, titanium, titanium-tungsten alloys, tungsten or molybdenum metal layers may be sputtered directly onto inner surface 75 or outer surface 80, with no thick films being disposed thereon.

In the sputtering step of the present invention, a DC magnetron sputtering technique is preferred, but RF sputtering techniques may less preferably be employed. A DC magnetron machine that may find application in the present invention is an Model 2011 DC magnetron sputtering device manufactured by ADVANCED ENERGY of Fort Collins Colo. A preferred thickness for second layers formed of gold is about 10,000 Angstroms. A preferred thickness for first layers formed of nickel is about 25,000 Angstroms.

Figure 3:
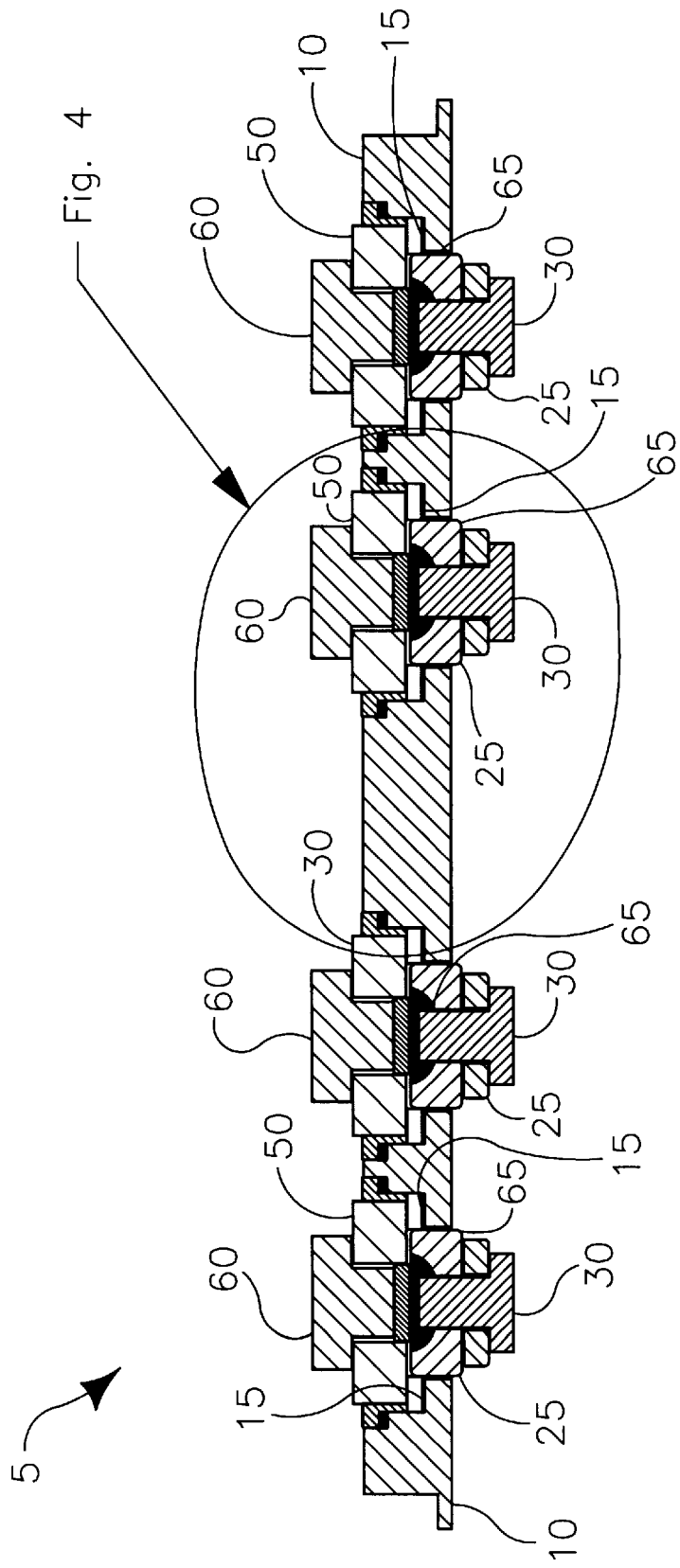
FIG. 3 shows a cross-sectional view of one embodiment of a multi-polar feedthrough assembly of the present invention.
Figure 4:
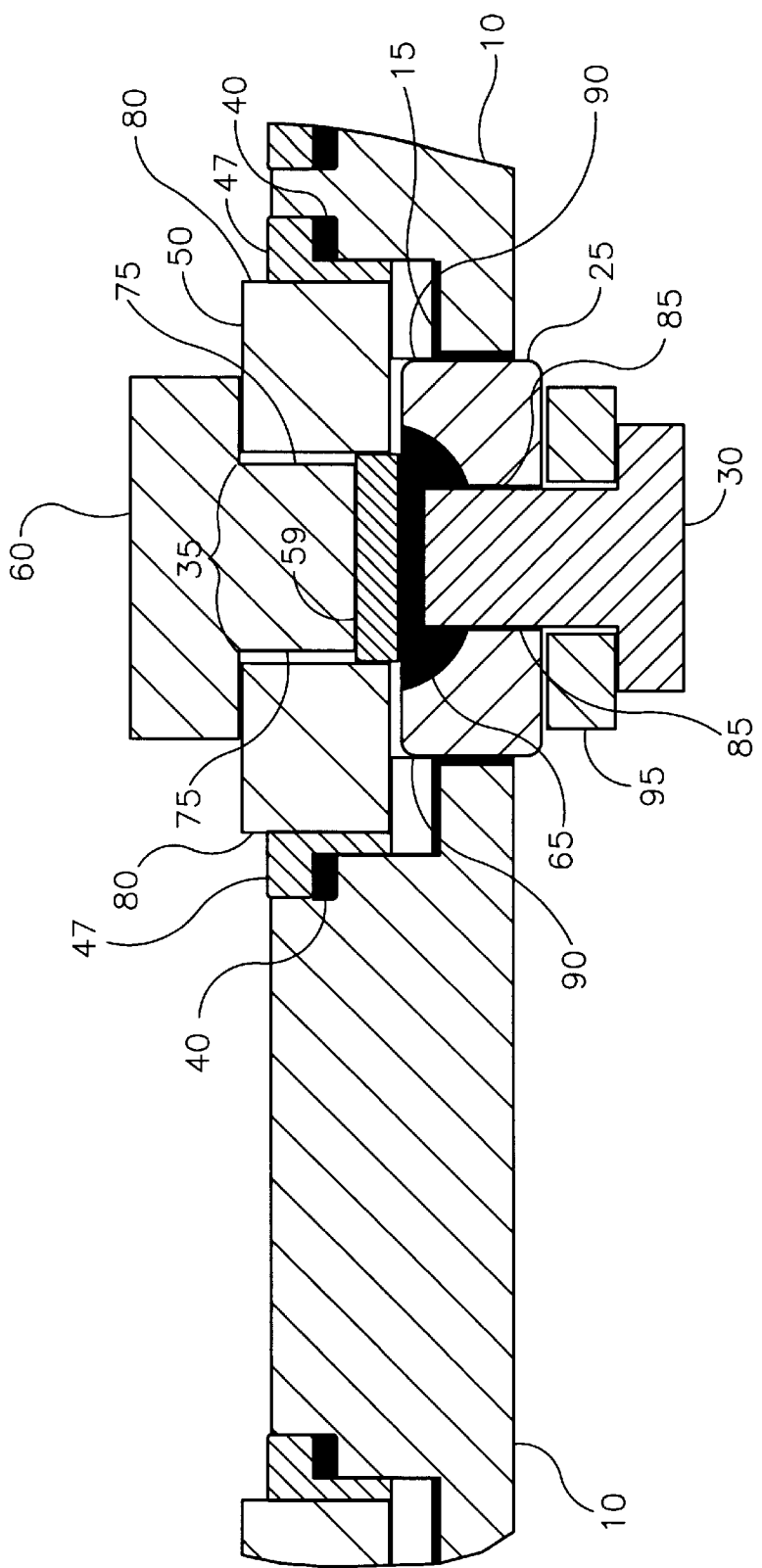
FIG. 4 shows an enlarged view of a portion of the multi-polar feedthrough assembly of FIG. 3.
Figure 5:
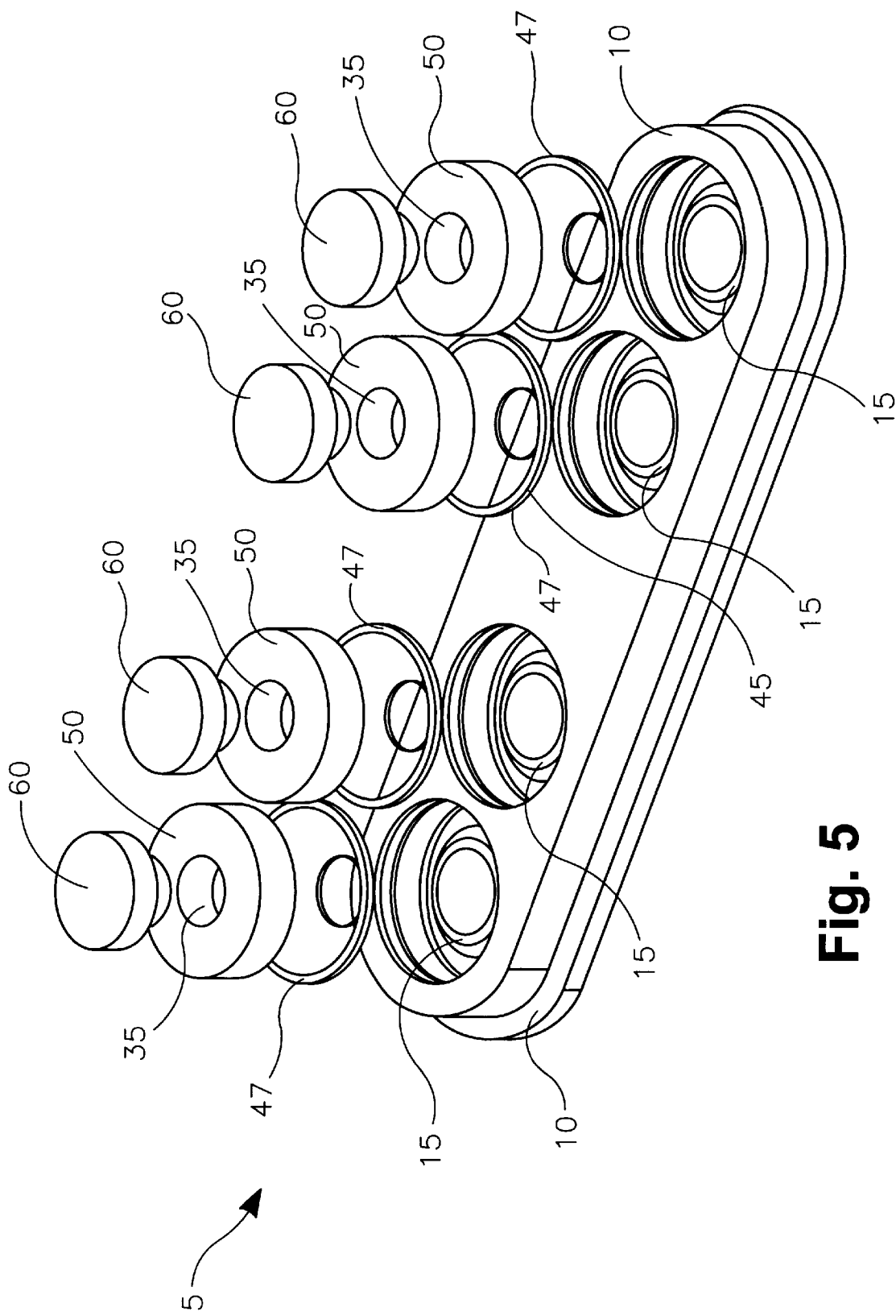
FIG. 5 shows an exploded perspective view of portions of the multi-polar feedthrough assembly of FIGS. 3 and 4.

FIG. 3 shows a cross-sectional view of one embodiment of multi-polar feedthrough assembly 5 of the present invention after being subjected to the adhesive application and brazing steps of the present invention. FIG. 4 shows an enlarged view of a portion of multi-polar feedthrough assembly 5 of FIG. 3. FIG. 5 shows an exploded perspective view of portions of multi-polar feedthrough assembly 5 of FIGS. 3 and 4.

In FIGS. 3, 4 and 5 a plurality of insulators 25, feedthrough pins 30, capacitive filters 50, contact pads 60 and other components are disposed directly in ferrule 10. Spacers or washers 95 in FIGS. 3 and 4 are optional, and need not, but may, be included in assembly 5 if the head portion of pin 30 is appropriately shortened.

Unitary multi-polar ferrule or cover 10 of FIGS. 3, 4 or 5 may be replaced with a plurality of separate ferrules that are disposed in and attached to a corresponding cover, substrate, container or shield. FIG. 4 shows inner braze joint 65, intermediate braze joint 15, outer braze joint 40, inner solder joint 55 and outer adhesive joint 45 of the present invention. It will now become apparent to those skilled in the art that many other embodiments and configurations of uni-polar and multi-polar feedthrough assemblies fall within the scope of the present invention, including those where inner solder joint 55 is replaced with or augmented by inner adhesive joint 55, outer adhesive joint 45 augments or is replaced by outer solder joint 45, and/or outer braze joint 40 is eliminated.

Figure 6:
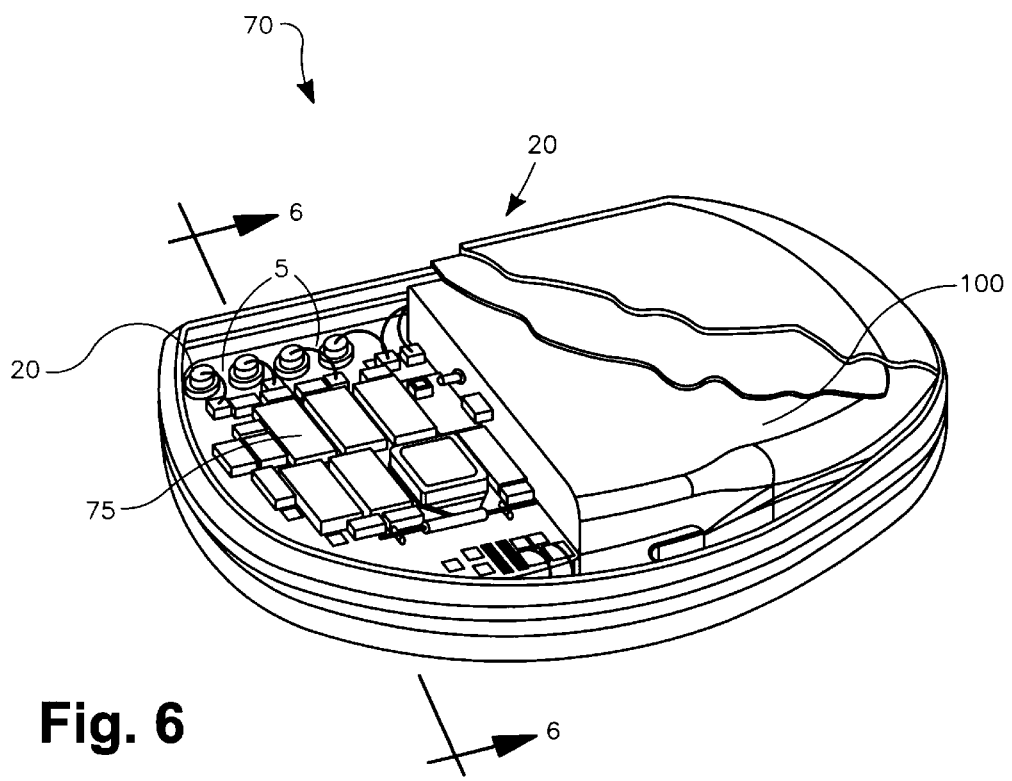
FIG. 6 shows a perspective, cut-away view of the internal components of an implantable medical device of the present invention.
Figure 7:
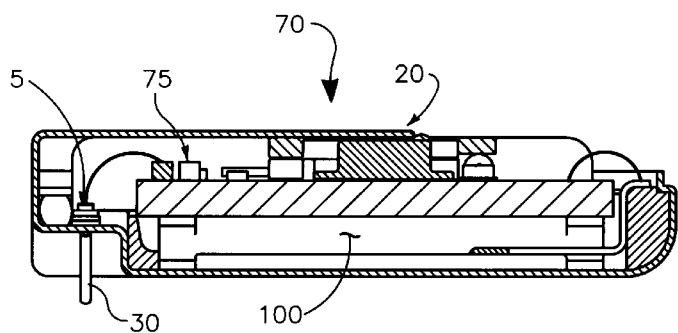
FIG. 7 shows a cross-sectional view of the implantable medical device of FIG. 6.

FIG. 6 shows a perspective, cut-away view of the internal components of one embodiment of implantable medical device 70 of the present invention. In FIG. 6, a generic implantable pulse generator (or IPG) 70 is shown. IPG 70 includes battery section 101, hybrid electronics section or internal circuitry 75, and feedthrough assembly 5, all enclosed by can, shield or container 20. Conductor materials for feedthrough assemblies 5 are most preferably selected on the basis of their reported stability when in contact with body fluids. Feedthrough assembly may comprise one or more feedthroughs, and provides a hermetic seal for device 70. FIG. 7 shows a cross-sectional view of the implantable medical device of FIG. 6.

In one adhesive application step of the present invention, the electrically conductive adhesive materials employed to form adhesive joints 47 and/or 57 must be heated to a temperature that most preferably does not exceed about 200 degrees Celsius to cure the adhesives after their application. A preferred curing temperature for ABLEBOND 8700E adhesive has been found to be about 175 degrees Celsius for a duration of about 1 hour. Maximum curing temperatures for suitable adhesives of the present invention are less than about 500 degrees Celsius and greater than about 15 degrees Celsius. A preferred range of adhesive curing temperatures of the present invention is between about room temperature and about 250 degrees Celsius. A preferred range of adhesive curing times or durations of the present invention is between about 1 minute and about 24 hours.

In a preferred method of the present invention, the adhesive application step occurs at room temperature, where feedthrough assembly 5 is held at room temperature while a suitable adhesive is applied to inner braze joint 65 and outer braze joint 45. Assembly 5 is then cured at elevated temperatures of about 175 degrees Celsius for about one hour, most preferably in a Model No. OV-12A oven provided by Blue M Electric Company of Blue Island, Ill.

In one brazing step of the present invention, the metals or alloys employed to form braze joints 15, 40 and 65 must be heated to a temperature exceeding about 500 degrees Celsius. In a preferred method of the present invention, the brazing step occurs at peak temperatures of about 1,090 degrees Celsius, where feedthrough assembly 5 is held and soaked at that peak temperature for about 40 seconds following a preferred heating ramp-up period of about 1 hour during which time assembly 5 is taken from room temperature to the peak temperature. Additionally, it is preferred that assembly 5 be pre-soaked at a temperature of about 1,050 degrees Celsius for about 2 minutes to stabilize temperatures throughout the brazing furnace and graphite fixture within which assembly 5 is held during the brazing step.

A preferred cooling ramp-down period following the peak temperature brazing period is also about one hour. Preferred ramp-up and ramp-down periods of the brazing step of the method of the present invention range between about 20 minutes and about 6 hours. The peak temperature of the brazing step of the method of the present invention is most preferably about 50 degrees Celsius above the melting temperature of the brazing metal or alloy selected, but may range as low as the melting temperature of the brazing metal or alloy selected.

A preferred furnace for the brazing step of the present invention is a Model No. 3040 WORKHORSE® furnace manufactured by VACUUM INDUSTRIES® of Sommerville, Mass. It is preferred that the brazing step of the present invention occur in a vacuum or inert atmosphere. If a vacuum is employed in the brazing step, pressures less than about $8 \times 10^{-5}$ Torr are preferred prior to initiating brazing. Much less preferably, and owing to the resultant excessive oxidation of the pin and ferrule, the brazing step of the present invention may occur in air or other non-inert atmosphere.

In a preferred method of the present invention, the soldering step occurs at peak temperatures of about 275 degrees Celsius, where feedthrough assembly 5 is held at that peak temperature for about 30 seconds following a preferred heating ramp-up period of about 5 minutes during which time assembly 5 is taken from room temperature to the peak temperature. Preferred ramp-up and ramp-down rates are about 5 degrees per second. A resistance heating soldering method is preferred in the present invention.

Prior to initiating soldering, it is preferred that air be removed from the solder chamber by a combined vacuum-backfill-exhaust procedure. First, a vacuum of about 30 inches mercury is achieved. Then the chamber is backfilled with nitrogen until a pressure of about 10 psig is attained. Finally, nitrogen gas is withdrawn from the chamber until atmospheric or ambient pressures are attained. Next, the foregoing vacuum-backfill-exhaust procedure is repeated several times, followed by the chamber being filled with nitrogen, the nitrogen being expelled until a pressure of about 5 psig is attained, and the chamber being held at that pressure.

A preferred cooling ramp-down period following the peak temperature soldering period is also about 5 minutes. Preferred ramp-up and ramp-down periods of the soldering step of the method of the present invention may range between about 20 seconds and about 10 minutes. The peak temperature of the soldering step of the method of the present invention is most preferably about 75 degrees Celsius above the melting temperature of the soldering metal or alloy selected, but may range as low as the melting temperature of the soldering metal or alloy selected.

A preferred furnace for the soldering step of the present invention is a Model DAP 2200 furnace manufactured by SCIENTIFIC SEALING, INC.® of Downey, Calif. It is preferred that the soldering step of the present invention occur in a vacuum, a nitrogen atmosphere or other inert atmosphere. Less preferably, and providing flux is employed in the soldering step, the soldering step of the present invention may occur in air or other non-inert atmosphere.

Figure 8:
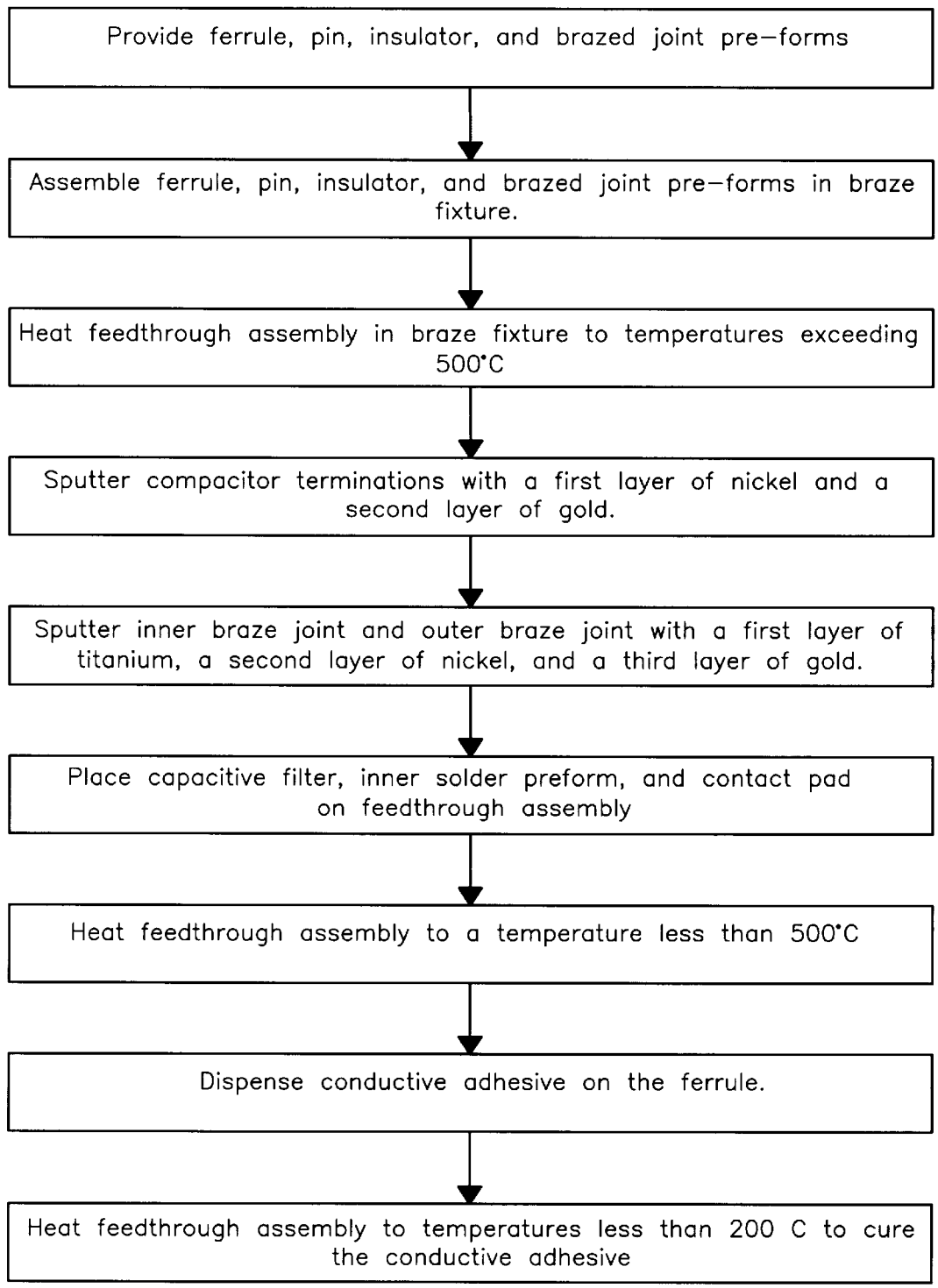
FIG. 8 shows a flow chart of one method of the present invention.

FIG. 8 shows a flow chart of one method of the present invention. In FIG. 8, ferrule or cover 10, pin 30, insulator 25, and braze joint pre-forms corresponding to inner braze joint 65, intermediate braze joint 15 and outer braze joint 40 are provided. The foregoing components are assembled in a braze fixture, most preferably in a graphite braze fixture. Next, assembled ferrule or cover 10, pin 30, insulator 25, and braze joint pre-forms corresponding to element 65 of the Figures, intermediate braze joint 15 and outer braze joint 40 are heated to an appropriate brazing temperature exceeding about 500 degrees Celsius in a brazing step to form a brazed feedthrough assembly.

Following the brazing step, at least one metal layer is disposed in inner surface 75 and outer surface 80 of capacitive filter 50 to facilitate attachment of capacitive filter 50 to outer adhesive joint 47 and/or outer solder joint 45 on the one hand, and inner adhesive joint 57 and/or inner solder joint 55 on the other hand. In a preferred method of the present invention, a first nickel layer and a second gold layer are sputtered successively onto thick films overlying inner surface 75 and outer surface 80.

Next, inner braze joint 65 and outer braze joint 40 are sputtered successively with a first layer of titanium, a second layer nickel and a third layer of gold. Capacitive filter 50, an inner solder joint preform corresponding to element 55 of the Figures and contact pad 60 are placed on or in the brazed feedthrough assembly, whereupon the so-combined feedthrough assembly is heated to a temperature less than about 500 degrees Celsius, most preferably in accordance with the methods and parameters described hereinabove respective soldering. In another method of the present invention, capacitive filter 50 and an outer solder joint preform corresponding to element 45 are placed on or in the brazed feedthrough assembly, whereupon the so-combined feedthrough assembly is heated to a temperature less than about 500 degrees Celsius, most preferably in accordance with the methods and parameters described hereinabove respective soldering.

A suitable electrically conductive adhesive may be applied in third aperture 35, which upon subsequent curing forms inner adhesive joint 55. Depending upon the structural configuration selected, the same or a different suitable electrically conductive adhesive may also be applied between outer braze joint 40 and outer surface 80 of capacitor 50, which upon subsequent curing forms outer adhesive joint 45. (In another method of the present invention, the same or a different suitable electrically conductive adhesive may be applied between intermediate braze joint 15 and outer surface 80 of capacitor 50, which upon subsequent curing forms outer adhesive joint 45.) The foregoing components, adhesives and brazed assembly are heated to an appropriate temperature, typically less than or equal to about 200 degrees Celsius in an adhesive curing step.

In the present invention, it has been discovered that under most circumstances it is difficult to apply a continuous, unbroken bead of adhesive between outer braze joint 40 and outer surface 80. Moreover, leaktightness testing of intermediate braze joint 15 may be compromised if a continuous bead of adhesive is employed to form adhesive joint 45. (Such a continuous bead might indicate leaktightness even though braze joint 15 is not leaktight.) For the foregoing reasons, and as illustrated in FIG. 2 hereof, adhesive joint 45 is most preferably formed by a plurality of adjoining strips or portions of adhesive. In like fashion, inner adhesive joint 55 may be formed from a plurality of adjoining strips or portions of adhesive.

Figure 9:
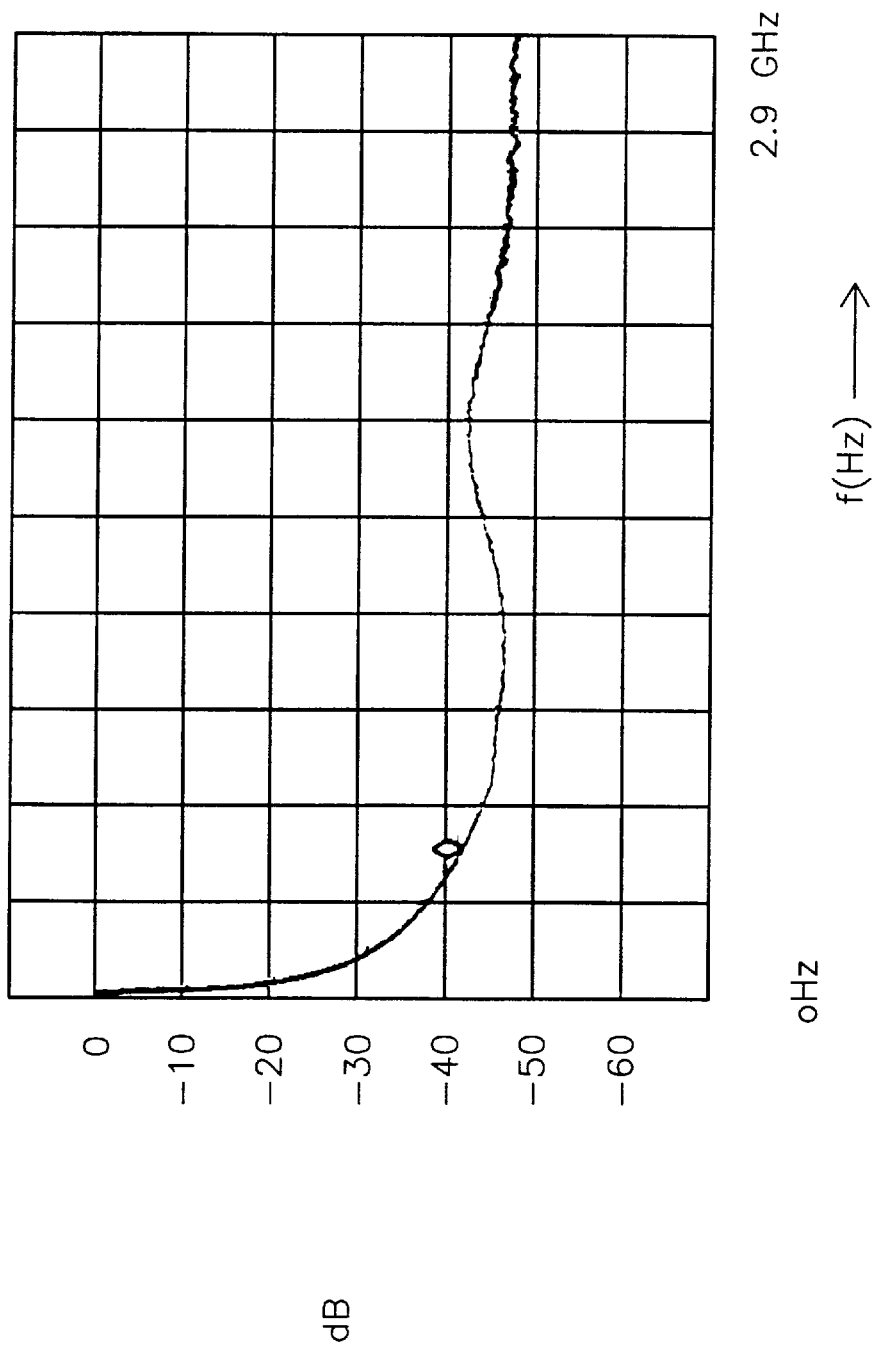
FIG. 9 shows graphs of EMI insertion loss data obtained with capacitive filter feedthroughs of the present invention.

FIG. 9 shows a graph of EMI insertion loss data obtained with capacitive filter feedthroughs of the present invention disposed within conventional pacemakers. FIG. 9 shows test results obtained employing one embodiment of the present invention, where a capacitive filter feedthrough contained gold braze joints or pads 15, 40 and 65 in combination with adhesive joint 45 and inner solder joint 55.

Insertion loss is a measurement of the attenuation of unwanted signals such as EMI. Insertion loss was measured using a spectrum analyzer that generated ac signals having frequencies ranging between 0 and 2.9 Gigahertz. Analyzer output signals were applied to feedthrough pins 30 by a first cable. The analyzer received input signals through a second cable connected to contact pad 60. We define insertion loss here as:

$$\text{insertion loss (db)} = 20\log_{10} \cdot \left(\frac{E_1}{E_2}\right) \quad \text{(eq. 1)}$$

where:
$E_1$=output voltage with feedthrough in the circuit
$E_2$=output voltage with feedthrough not in the circuit The insertion loss curves of FIG. 9 were generated by sweeping test frequencies between 0 and 2.9 Gigahertz and simultaneously measuring insertion loss. FIG. 9 shows that feedthrough assemblies of the present invention attenuate EMI significantly.

Although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims. For example, any one of inner adhesive joint 55, outer adhesive joint 45, intermediate braze joint 15, inner braze joint 65, outer braze joint 40, inner solder joint 55 or outer solder joint 45 of the present invention may be replaced with a suitable electrically conductive plastic or polymer containing or blended with silver flakes or a suitable electrically conductive epoxy or filler. Or, any of the various possible combinations that may be formed by combining two or more of inner adhesive joint 55, outer adhesive joint 45, intermediate braze joint 15, inner braze joint 65, outer braze joint 40, inner solder joint 55 and outer solder joint 45 may be employed in the present invention.

The scope of the present invention is not limited to pacing, monitoring or sensing applications, but extends to defibrillation, cardiac mapping and other medical and medical device applications and methods. The scope of the present invention is not limited to applications where a human heart is sensed, monitored, paced, or defibrillated, but includes similar applications in other mammalians and mammalian organs.

The preceding specific embodiments are illustrative of the practice of the invention. It is to be understood, therefore, that other expedients known to those skilled in the art or disclosed herein, may be employed without departing from the invention or the scope of the appended claims.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents listed in Table 1 or elsewhere hereinabove are hereby incorporated by reference into the specification hereof, each in its respective entirety.

We claim:

1. A feedthrough assembly for an implantable medical device, comprising:
   (a) an electrically conductive ferrule having a first aperture disposed therethrough, the first aperture having first sidewalls; the ferrule being formed of at least one of titanium, niobium, platinum, molybdenum, zirconium, tantalum, vanadium, tungsten, iridium, rhodium, rhenium, osmium, ruthenium, palladium, silver, and alloys, mixtures and combinations thereof;
   (b) an insulator having a second aperture disposed therethrough, the second aperture having second sidewalls, the insulator being disposed within the first aperture and being formed of a ceramic-containing, electrically insulative material;
   (c) an electrically conductive pin having upper and lower portions, at least the upper portion of the pin extending into the second aperture, the pin being formed of at least one of titanium, niobium, platinum, molybdenum, zirconium, tantalum, vanadium, tungsten, iridium, rhodium, rhenium, osmium, ruthenium, palladium, silver, and alloys, mixtures and combinations thereof;
   (d) an electrically conductive inner braze joint disposed atop the upper portion of the pin or between the pin and the second sidewalls of the second aperture, to form a seal therebetween, the inner braze joint being formed of at least one of: (1) pure gold; (2) a gold alloy comprising gold and at least one of titanium, niobium, vanadium, nickel, molybdenum, platinum, palladium, ruthenium, silver, rhodium, osmium, iridium, and alloys, mixtures and thereof; (3) a copper-silver alloy comprising copper, silver and optionally at least one of iridium, titanium, tin, gallium, palladium, platinum, and alloys, mixtures and combinations thereof; and (4) a silver-palladium-gallium alloy;
   (e) an electrically conductive intermediate braze joint disposed between the insulator and the first sidewalls of the first aperture to form a seal therebetween, the intermediate braze joint being formed of one or more of: (1) pure gold; (2) a gold alloy comprising gold and at least one of titanium, niobium, vanadium, nickel, molybdenum, platinum, palladium, ruthenium, silver, rhodium, osmium, iridium, and alloys, mixtures and thereof; (3) a copper-silver alloy comprising copper, silver and optionally at least one of iridium, titanium, tin, gallium, palladium, platinum, and alloys, mixtures and combinations thereof; and (4) a silver-palladium-gallium alloy;
   (f) a ceramic-containing capacitive filter having one of a third aperture and a passageway disposed therethrough, a first electrical terminal being disposed within, contiguous with or propinquant to the third aperture or passageway, a second electrical terminal being disposed on or propinquant to an outer surface of the capacitive filter;
   (g) an electrically conductive inner adhesive joint or inner solder joint disposed within the third aperture or the passageway, the inner adhesive joint or inner solder joint being electrically and mechanically connected to the inner braze joint or the first terminal, the inner solder joint being formed of at least one of: (1) an indium-lead alloy; (2) indium only; (3) lead only; (4) silver only; (5) tin only; (6) an indium-silver alloy; (7) an indium-tin alloy; (8) a tin-lead alloy; (9) a tin-silver alloy; (10) an indium-lead-silver alloy; (11) a tin-lead-silver alloy; (12) a gold-tin alloy; (13) a gold-silicon alloy; (14) a gold-germanium alloy; and (15) a gold-indium alloy, and (I) an electrically conductive outer adhesive joint or outer solder joint disposed between the ferrule and the second electrical terminal, the outer adhesive joint or outer solder joint electrically and mechanically connecting the ferrule to the second terminal, the outer solder joint being formed of at least one of: (1) an indium-lead alloy; (2) indium only; (3) lead only; (4) silver only; (5) tin only; (6) an indium-silver alloy; (7) an indium-tin alloy; (8) a tin-lead alloy; (9) a tin-silver alloy; (10) an indium-lead-silver alloy; (11) a tin-lead-silver alloy; (12) a gold-tin alloy; (13) a gold-silicon alloy; (14) a gold-germanium alloy; and (15) a gold-indium alloy;

wherein the capacitive filter, in combination with the electrical connections established to the first and second terminals thereof from, respectively, the pin and the ferrule, attenuates electromagnetic interference when installed in an implantable medical device.

2. The feedthrough assembly of claim 1, wherein an electrically conductive outer braze joint is disposed between the ferrule and the outer surface of the capacitive filter, the outer braze joint being formed of at least one of: (1) pure gold; (2) a gold alloy comprising gold and at least one of titanium, niobium, vanadium, nickel, molybdenum, platinum, palladium, ruthenium, silver, rhodium, osmium, iridium, and alloys, mixtures and thereof; (3) a copper-silver alloy comprising copper, silver and optionally at least one of iridium, titanium, tin, gallium, palladium, platinum, and alloys, mixtures and combinations thereof; and (4) a silver-palladium-gallium alloy.

3. The feedthrough assembly of claim 1, wherein the capacitive filter is disposed at least partially in the first aperture.

4. The feedthrough assembly of claim 1, wherein a lower surface of an electrically conductive contact pad is electrically and mechanically connected to the inner adhesive joint or inner solder joint, the contact pad having an upper surface suitable for wirebonding, soldering, gluing, welding, laser welding, or brazing an electrical connection thereon or thereto.

5. The feedthrough assembly of claim 4, wherein the contact pad is formed of one of: (a) having first a layer of nickel and then a layer of gold disposed on the surface thereof; (b) brass having first a layer of nickel and then layer of gold disposed on the surface thereof; (c) pure gold; (d) nickel having a layer of gold disposed on the surface thereof, and (e) pure copper or copper alloy having first a layer of nickel and then a layer of gold disposed on the surface thereof.

6. The feedthrough assembly of claim 4, wherein the contact pad is electrically connected to internal circuitry disposed within an implantable medical device.

7. The feedthrough assembly of claim 1, wherein an hermetic seal is provided between the ferrule and the capacitive filter by at least one of the outer braze joint, the outer adhesive joint or the outer solder joint.

8. The feedthrough assembly of claim 1, wherein an hermetic seal is provided between the insulator and the pin by at least one of the inner braze joint, the inner adhesive joint or the inner solder joint.

9. The feedthrough assembly of claim 1, wherein a hermetic seal is provided between the insulator and the first aperture by the intermediate braze joint.

10. The feedthrough assembly of claim 1, wherein the ferrule is electrically and mechanically connected to one of a housing, container, cover, and shield in an implantable medical device.

11. The feedthrough assembly of claim 1, wherein the ferrule forms a portion of, and is structurally unitary in respect of, one of a housing, container, cover, case and shield in an implantable medical device.

12. The feedthrough assembly of claim 1, wherein the implantable medical device is one of a pacemaker, an implantable pulse generator, a defibrillator, a pacemaker-cardioverter-defibrillator, a neurological stimulator and a gastro-intestinal stimulator.

13. The feedthrough assembly of claim 1, wherein the pin is electrically connected to one of a connector block and a connector located outside the implantable medical device.

14. The feedthrough assembly of claim 1, wherein the capacitive filter is a discoidal capacitor.

15. The feedthrough assembly of claim 1, wherein the capacitive filter is a multi-layer capacitor.

16. The feedthrough assembly of claim 1, wherein the capacitive filter comprises barium titanate.

17. The feedthrough assembly of claim 1, wherein the capacitive filter is selected from the group consisting of single-layer capacitors, rectangular capacitors, square capacitors, elliptical capacitors, and oval capacitors.

18. The feedthrough assembly of claim 1, wherein the capacitive filter has at least one of a silver thick film, a silver-palladium alloy thick film, and a silver-platinum alloy thick film disposed on the inner capacitive filter surface or outer capacitive filter surface thereof.

19. The feedthrough assembly of claim 17, wherein the capacitive filter has at least one nickel or gold layer sputtered onto the thick film surfaces thereof.

20. The feedthrough assembly of claim 1, wherein at least one of niobium, titanium, titanium-tungsten alloy, tungsten and molybdenum are sputtered onto an inner surface or an outer surface of the insulator.

21. A feedthrough assembly for an implantable medical device, comprising:

(a) means for forming an electrically conductive ferrule having a first aperture disposed therethrough, the first aperture having first sidewalls;

(b) means for insulating having a second aperture disposed therethrough, the second aperture having second sidewalls, the insulating means being disposed within the first aperture and being formed of a ceramic-containing, electrically insulative material;

(c) means for forming an electrically conductive pin having upper and lower portions, at least the upper portion of the pin forming means extending into the second aperture;

(d) means for forming an electrically conductive inner braze joint disposed atop the top portion of the pin means and between the pin forming means and the second sidewalls of the second aperture to form a seal therebetween;

(e) means for forming an electrically conductive intermediate braze joint disposed between the insulating means and the first sidewalls of the first aperture to form a seal therebetween;

(f) a means for capacitively filtering having one of a third aperture and a passageway disposed therethrough, a first electrical terminal being disposed within or propinquant to the third aperture or passageway, a second electrical terminal being disposed on an outer surface of the capacitive filtering means;

(g) means for forming an electrically conductive inner adhesive joint or inner solder joint disposed within or propinquant to the third aperture or the passageway, the inner adhesive or solder joint forming means being electrically and mechanically connected to the inner braze joint forming means or the first terminal;

(h) an electrically conductive means for forming an outer adhesive joint or an outer solder joint disposed between the ferrule forming means and the second electrical terminal, the outer adhesive or solder joint forming means electrically and mechanically connecting the ferrule forming means and the second terminal;

wherein the capacitive filtering means, in combination with the electrical connections established to the first and second terminals thereof from, respectively, the pin forming means and the ferrule forming means, attenuates electromagnetic interference when installed in an implantable medical device.

22. The feedthrough assembly forming means of claim 21, wherein an electrically conductive means for forming an outer braze joint is disposed between the ferrule and the outer surface of the capacitive filtering means.

* * * * *

UNITED STATES PATENT AND TRADEMARK OFFICE
CERTIFICATE OF CORRECTION

PATENT NO.    : 6,031,710
DATED         : February 29, 2000
INVENTOR(S)   : William D. Wolf, Mary A. Fraley, Lynn M. Seifried and Ronald F. Hoch It is certified that error appears in the above-identified patent and that said Letters Patent is hereby corrected as shown below:

Column 17,
Line 51: "(a) having" should be "(a) an iron-nickel-cobalt alloy having"

Signed and Sealed this

Twenty-first Day of August, 2001

Attest:

NICHOLAS P. GODICI
*Attesting Officer*          *Acting Director of the United States Patent and Trademark Office*